United States Patent [19]
Liu et al.

[11] Patent Number: 5,908,771
[45] Date of Patent: Jun. 1, 1999

[54] METHOD FOR REGENERATION OF SALVIA SPECIES

[75] Inventors: Wennuan Liu; Gary Mark Hellmann, both of Clemmons; Richard Carlton Reich, Winston-Salem, all of N.C.

[73] Assignee: R. J. Reynolds Tobacco Company, Winston-Salem, N.C.

[21] Appl. No.: 08/792,081

[22] Filed: Jan. 31, 1997

[51] Int. Cl.⁶ .............................. A01H 4/00; C12N 15/82
[52] U.S. Cl. ....................... 435/172.3; 435/419; 435/430; 435/431; 800/DIG. 67
[58] Field of Search .................. 435/172.3, 419, 435/430, 431; 800/DIG. 67

[56] References Cited

U.S. PATENT DOCUMENTS

| | | | |
|---|---|---|---|
| 5,177,306 | 1/1993 | Whitaker | 800/200 |
| 5,304,725 | 4/1994 | Nelson | 800/200 |
| 5,477,000 | 12/1995 | Saxena et al. | 435/430 |

FOREIGN PATENT DOCUMENTS

| | | |
|---|---|---|
| 1-218582 | 8/1989 | Japan . |

OTHER PUBLICATIONS

Xu et al. Transformation *in Salvia chinensis* in Biotechnology in Agriculture and Forestry, vol. 22; Plant Protoplasts and Genetic Engineering III (ed. by Y.P.S. Baja). Springer–Verlag, Berlin, Feb. 1994.

Morimoto et al. Production of lithospermic acid B and rosmarinic acid in callus tissue and regenerated plantlets of *Salvia miltiorrhiza*. Journal of Natural Products. 57(6):817–823, Jun. 1994.

Shimomura et al. Tanshinone production in adventitious roots and regenerates of *Salvia miltiorrhiza*. Journal of Natural Products. 54(6):1583–1587, Nov–Dec. 1991.

Hu et al. Diterpenoid production in hairy root cultures of *Salvia miltiorrhiza*. Phytochemistry. 32(3):699–703, Feb. 1993.

Bugara et al. Embryoidogenesis in anther culture of *Salvia sclarea*. Fiziologiia i biokhimiia kul'turnykh rastenii. 18(4):381–386, Jul–Aug. 1986.

Bugara et al. *Haploid callusogenesis* in the culture on unfertilized ovules of Salvia sclarea. Fiziologiia i biokhimiia kul'turnyk rastenii. 21(6):554–560, 1989.

Pogorel'skaya, A. et al., *Tsitologiya i Genetika*, vol. 19, No. 5, pp. 364–367 (1985).

Shamam, a. et al., *Cromap*, vol. 7, No. 1, pp. 39–48 (1985).

Trudy, *Vsesoiuznyi nauchno–issledovatel'skii institut efi-mormaslichnykh kul'tur*, vol. 16, pp. 84–86 (1984). (with translation).

*Primary Examiner*—Douglas W. Robinson
*Assistant Examiner*—Thanda Wai
*Attorney, Agent, or Firm*—Myers Bigel Sibley & Sajover

[57] ABSTRACT

Salvia is regenerated via organogenesis using plant tissue culture techniques in a multistage culturing process. Roots can be induced from regenerated shoots, and the regenerated plants can be transferred to soil for further growth after the root system is well established.

7 Claims, 12 Drawing Sheets

METHOD FOR REGENERATION OF SALVIA SPECIES

FIELD OF THE INVENTION

The present invention provides methods for regenerating species of Salvia, such as clary sage (*Salvia sclarea*), via organogenesis and plant tissue culture. More specifically, it relates to the use of exogenous plant growth regulators and specific explant tissues to establish organogenic lines of galvia and to reproduce Salvia plants, including genetically transformed Salvia plants.

BACKGROUND OF THE INVENTION

The Salvia genus (family Lamiaceae) contains about 700 members that can be found in the tropical and temperate zones of the world, with about 300 species distributed in Asia, Europe and Africa and 400 in America (Willis J C (1966) *A Dictionary of Flowering Plants and Ferns*, 7th Edn., Cambridge, University Press; Briquet J, (1897) Labiatae, In: *Die Naturlichen Pflanzenfamilien*, Engler and Prantl (Eds.), Vol. IV, 3a, pp. 183–375, Englemann, Leipzig). Numerous varieties of sage species, including varieties of *S. sclarea*, are known. Clary sage (*S. sclarea*) is native to the Mediterranean region, has been found growing in the wild, and is cultivated in a number of countries. *S. sclarea* occurs as an annual (rare), biennial (fairly common) or perennial (fairly common) open-pollinated herbaceous plant that has typical quadrangular stems, opposite leaves and verticillaster inflorescence.

Clary sage is cultivated mainly for the production of essential oil, sclareol and sclareol derivatives. U.S. Pat. No. 3,060,172 describes a process for the isolation of sclareol from clary sage; U.S. Pat. Nos. 5,525,728 and 5,247,100 describe processes for the production of sclareolide from sclareol. Sclareol and sclareol derivatives have been used as major perfume components, in flavoring foodstuffs, in wine making and as components of cigarette flavors. The main areas of commercial production of clary sage are the former Soviet Union, USA, France, China, Bulgaria, Hungary and India. Sage oil and sclareol are produced mainly in flower spikes; about 97 percent of the sclareol is located in the flower spikes, where it is synthesized exclusively in trichomes (the epidermal appendages or hairs) located on the inflorescence organs. The yield of clary sage oil and sclareol is subject to wide fluctuations, depending primarily on weather and soil conditions.

Although conventional plant breeding has played an important role in the improvement of clary sage, the yields of the aforementioned sage related products from such plants are still very low. A method of regenerating Salvia plants would be of assistance in the cultivation of sage and the production of clary sage oil and sclareol, as well as providing tissues and systems for transforming Salvia to provide genetically improved plants. It is therefore desirable to devise methods of regenerating species of Salvia, to provide organogenic lines of Salvia tissues and to reproduce Salvia plants.

SUMMARY OF THE INVENTION

A first aspect of the present invention is a method of producing organogenic tissues from a plant of the genus Salvia, by first obtaining an immature zygotic embryo cotyledon (IZEC) explant of a Salvia plant and then culturing the explant on an initiation medium comprising nutrients and at least one plant growth regulator under conditions sufficient to cause production of organogenic tissues (e.g., until organogenic tissues are produced).

A further aspect of the present invention is a method of regenerating a plantlet of the genus Salvia, by obtaining an immature zygotic embryo cotyledon (IZEC) explant of a Salvia plant and culturing the explant on an initiation medium under conditions sufficient to cause production of organogenic tissues (e.g., until organogenic tissues are produced). The organogenic tissue is then cultured on a shoot initiation medium under conditions sufficient to cause formation of at least one shoot (e.g., until a shoot is produced); and the shoot is then cultured on a root initiation medium to provide a Salvia plantlet.

A further aspect of the present invention is a method of proliferating organogenic tissues of the genus Salvia, comprising obtaining an immature zygotic embryo cotyledon (IZEC) explant of a Salvia plant and culturing the explant on an initiation medium under conditions sufficient to cause production of organogenic tissues (e.g., until organogenic tissues are produced). A growth of subcultured organogenic tissue is then isolated and subcultured on a proliferation medium to provide a line of organogenic tissues.

A further aspect of the present invention is a plurality of genetically identical organogenic tissues of the genus Salvia.

DETAILED DESCRIPTION OF THE INVENTION

Figure 1:
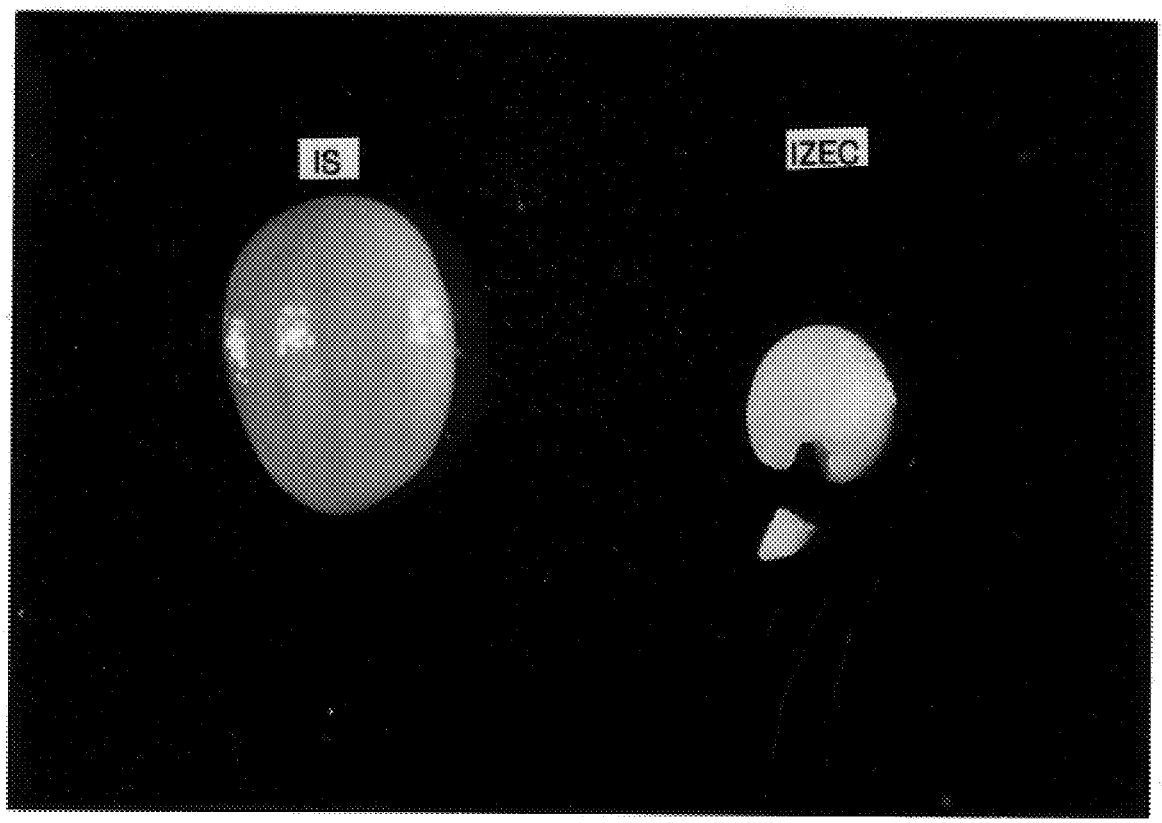
FIG. 1 shows an immature zygotic embryo cotyledon (IZEC) explant from an immature seed (IS) of *S. sclarea* (clary sage).

The term regeneration refers to the reproduction of a whole plant from a portion of tissue (an explant) or from somatic cells via asexual processes. There are two pathways of regeneration of plants in tissue culture: somatic embryogenesis and organogenesis. Somatic embryogenesis is a process resulting in the formation of embryos from somatic cells. The embryos can germinate to become a plant with both shoots and roots. Organogenesis is a process resulting in the formation of an organ, such as a shoot that later develops roots to produce a complete plant, and vice versa (Brown and Thorpe (1986) Plant regeneration and organogenesis; In: *Cell culture and somatic cell genetics of plants*, I. K. Vesil (ed), Academic Press, pp. 49–65).

Plant regeneration may be obtained by placing an explant on a nutrient medium supplemented with plant growth regulators. Plant tissue with competent cells responding to growth regulators can be used as explants; leaf and cotyledon tissues are most often used. Since Murashige and Skoog established the first complete nutrient medium for plant tissue culture in 1962, a number of new medium recipes have been developed and used for different species with different explants (Murashige and Skoog (1962) *Physiologia Plantarum* 15:473–493; George et al., (1987) *Plant culture media*, Vol. 1, Exegentics Limited, Wilts. BA13 4QG, England).

Plant growth regulators are exogenously supplied synthetic plant hormones, including but not limited to: auxins, cytokinins, gibberellic acid ($GA_3$) and abscisic acid (ABA). Auxins, including but not limited to, 2-naphthylacetic acid (NAA), indole-3-acetic acid (IAA), 2,4-dichlorophenoxyacetic acid (2,4-D) and indole butyric acid (IBA), promote cell division and growth. They may be utilized for somatic embryo initiation and root induction. Cytokinins, such as $N^6$-benzylaminopurine or $N^6$-benzyladenine (BA), promote cell division, affect the organization of dividing cells and may be used to stimulate shoot initiation. $GA_3$ can be used for shoot elongation and ABA for maturation of embryos in tissue culture.

Plant regeneration has been widely used for genetic transformation, plant propagation and creating somaclonal variation. A number of plant species have been transformed with heterologous genes, including the genes controlling flower development (Weigel and Nilsson (1995) *Nature* 377:495–500; Mandel and Yanofsky (1995) *Nature* 377:522–524), and some of these plants have been commercialized (Mazur B. (1995) *Trends in Biotechnology* 13:319–323). All of these processes utilized plant regeneration procedures. Using somaclonal variation, Whitaker and Burlington have developed a number of *Nicotiana glutinosa* lines with significantly increased sclareol levels (U.S. Pat. No. 5,177,306 to Whitaker) (all U.S. patents referenced herein are intended to be incorporated in their entirety herein). One of the lines showed a 2.5-fold increase in sclareol over the highest control.

Several species in the Salvia genus have been regenerated, including *S. milliorrhiza* (Li et al., (1988) *Recent Adv. Biotechnol. Appl. Biol*: 771–778; Shimonmura et al., (1991) *J. Natural Products* 54:1583–1587; Morimoto et al., (1994) *J. Natural Products* 57:817–823), *S. leucantha* (Hosoki and Tahara (1993) *Hortscience* 28:226), *S. greggii* (Frett, (1986) *Hortscience* 21(Sect.2):859; Frett, (1987) *Plant Cell Tissue Organ Culture* 9:89–93), *S. canariensis* L. (Mederos, (1991) *In Vitro* 27 (3) (Pt. 2): 133A), and *S. officinalis* (Olszowska and Furmanowa, (1990) *Planta Med.* 56:637). Meshcheriakova ((1984) *Vsesoiuznyi nauchnoissledovatel'skii institute firnomaslichnyky kul'tur* 16:84–86) reported the use of isolated meristem culture for clonal micropropagation of *Salvia sclarea*. However, an established plant regeneration system has not been available in *S. sclarea*.

Figure 2A:
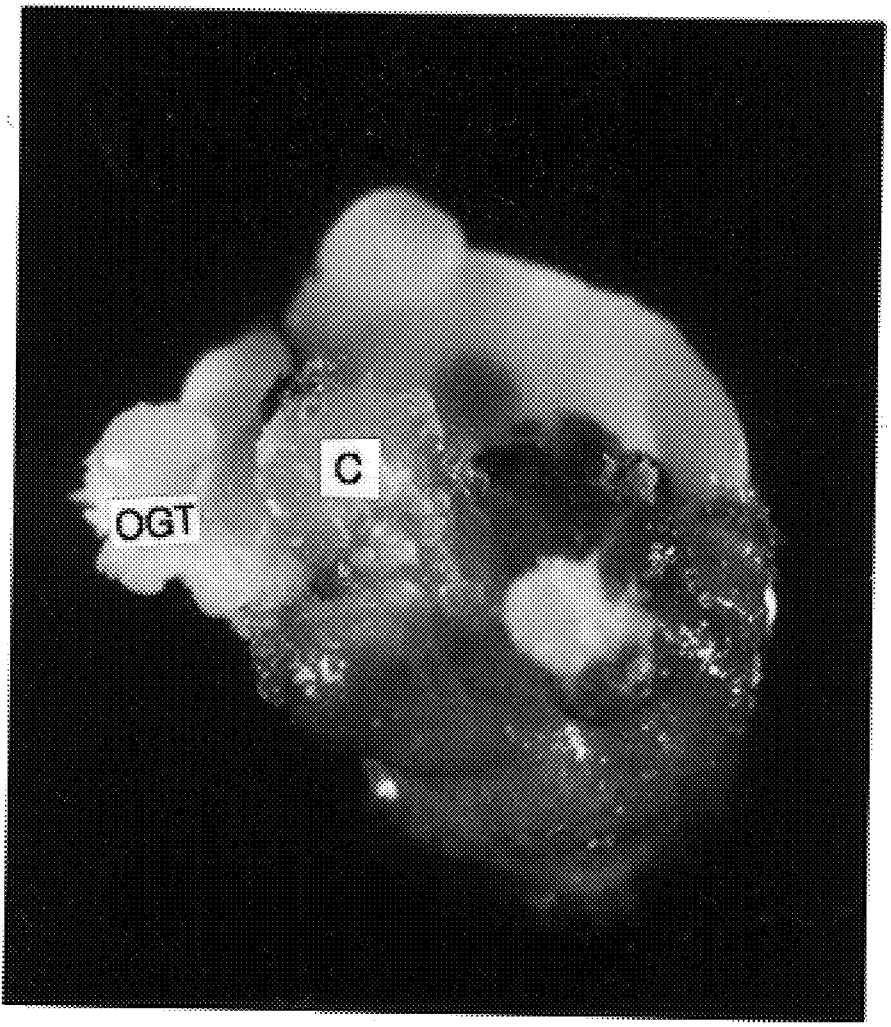
FIG. 2a shows organogenic tissues (OGT) and callus (C) induced from *S. sclarea* IZEC.
Figure 4A:
FIG. 4a shows green organogenic lines of *S. sclarea*.
Figure 4B:
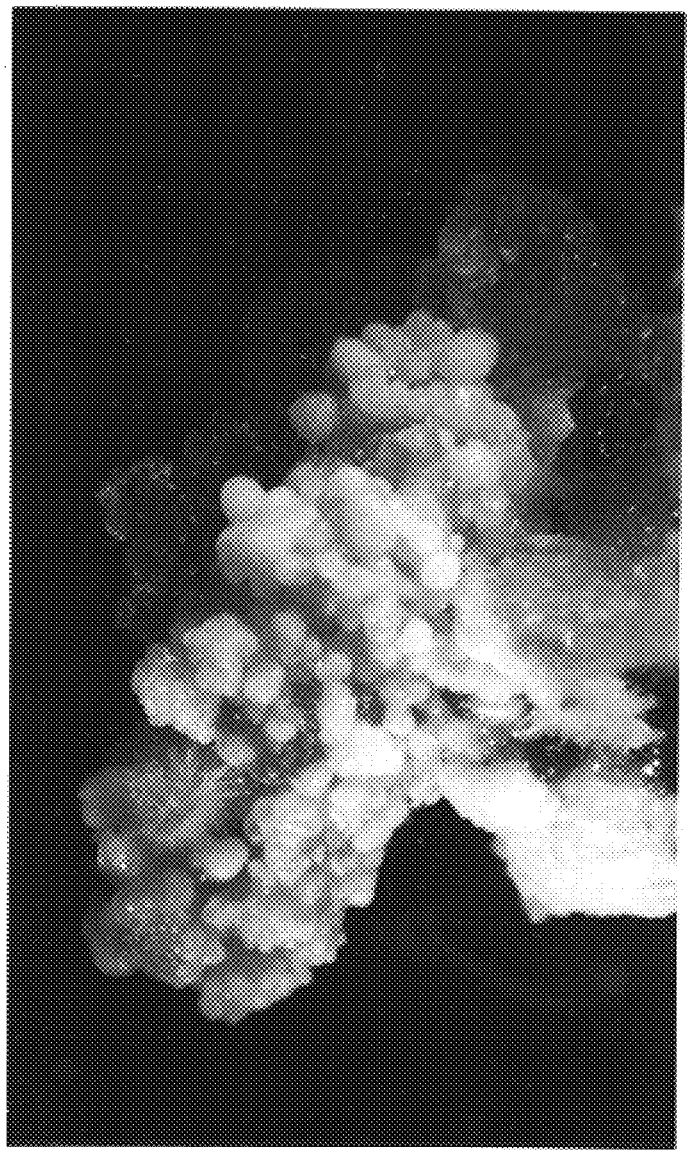
FIG. 4b shows white organogenic lines of *S. sclarea*.
Figure 5:
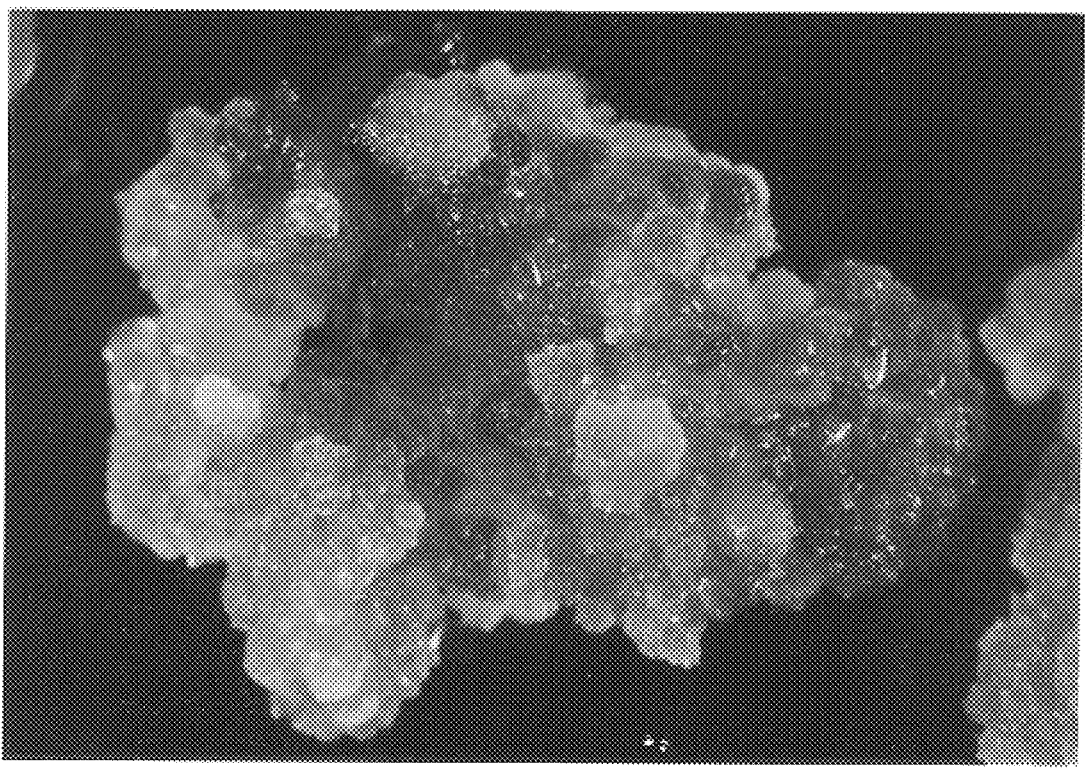
FIG. 5 shows organogenic callus of regenerated *S. sclarea*.
Figure 6:
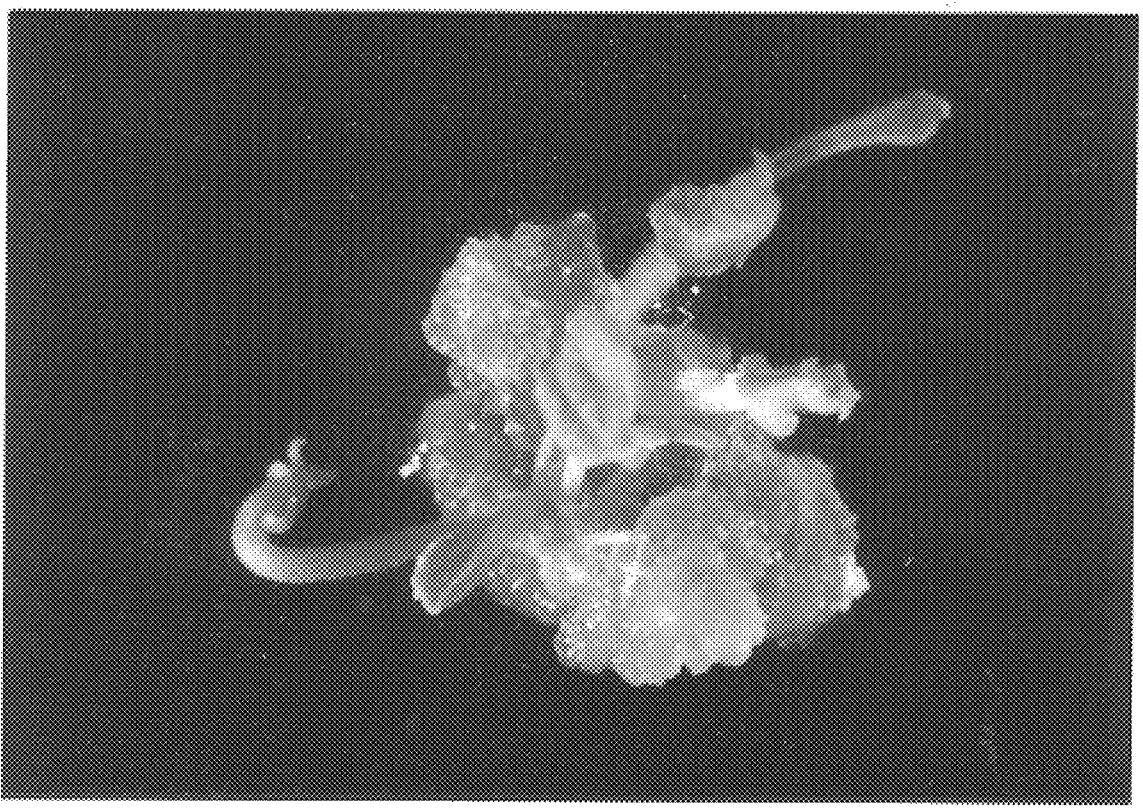
FIG. 6 depicts an early stage *S. sclarea* shoot developed from organogenic tissues.

The present invention provides a dependable method for the regeneration of Salvia species, including *S. sclarea*, via organogenesis and using plant tissue culture techniques. The method comprises the following stages: 1) obtaining suitable explant material from plants to be regenerated; 2) initiation of organogenic tissues and callus; 3) optional proliferation of organogenic tissues and callus and establishment of organogenic lines; and 4) shoot initiation and proliferation. Regenerated or proliferated shoots may then be separated and transferred to a rooting medium to provide individual plantlets (plantlets are small plants, i.e., they have the same essential structure as mature plants and are distinguished from, for example, regenerated shoots which lack roots). As used herein the term callus refers to an irregular mass of relatively is undifferentiated cells, which can arise from a single cell in tissue culture, as is known in the art and as shown in FIGS. 2a and 5. As used herein, organogenic tissues refer to those tissues capable of being induced to undergo organogenesis, that is, to form a plant organ such as shoot which can then be induced to develop roots to produce a complete plant. Organogenic tissues are shown in FIGS. 2a, 2b, 4a, 4b and 5.

In the first stage, a suitable Salvia genotype may be grown in the greenhouse or field. A cold treatment can optionally be applied to plants grown in the greenhouse to stimulate bolting and flowering. A human-facilitated pollination method may be employed during flowering to ensure seed production from greenhouse-grown plants. In the present methods, seeds are used as the source of explants, and immature seeds are preferred. A preferred explant for use in the present methods is the immature zygotic embryo cotyledon (IZEC). As used herein, the term "immature seed" refers to seeds which do not contain a mature plant embryo which is capable of germination; mature seeds are usually brown in color and found outside the parent plant, whereas immature seeds may still be retained within the parent plant. Immature Salvia seeds are typically those from one to four weeks after flowering or pollination.

IZEC explants may be obtained by removing the seed coat of a seed to reveal the plant embryo, and removing all of the embryo axes to leave only the immature zygotic embryo cotyledon. The term 'immature embryo' refers to embryos still in the early developmental stages, for example, from seeds which are still retained by the parent plant. The plant embryo typically proceeds through multiple definable stages, from the single cell stage, to a globular stage consisting of multiple cells, to the "heart-shaped stage" (a term familiar to those in the art), the "torpedo" stage, the cotyledon stage, and finally the mature embryo. IZEC explant tissue is preferably obtained from the heart-shaped, torpedo, or cotyledon stage. Because the embryo axes may be difficult to distinguish from embryo cotyledons in the heart-shaped and torpedo stages, it is most preferred to obtain IZEC explants from the embryonic cotyledon stage.

In the second stage, an IZEC explant (preferably aseptic) is placed on a suitable initiation medium. A suitable medium is composed of basic nutrients and at least one plant growth regulator at a sufficient concentration to support and promote cell growth, cell division and cell differentiation and organization. Modified MS basal medium (Table 1) as a nutrient supply with 2,4-D or BA (Table 2) as growth regulators are presently preferred. Either shoots, organogenic tissues or callus, depending on the type and concentrations of growth regulators used, will be produced under continuous culture.

In the third stage, the organogenic tissues and callus may be further proliferated under different regimes of plant growth regulators (proliferation medium) to develop organogenic lines for maintaining a constant supply of tissues for shoot initiation. As used herein, an organogenic line of tissue refers to a plurality of growths of organogenic tissues which have the same genotype and are capable of producing plant organs or organ-like structures. As used herein, proliferating an organogenic line of tissue refers to producing a plurality of genetically identical growths of organogenic tissue.

In the fourth stage shoots are induced on a shoot initiation medium, either from organogenic tissues initiated in the second stage or from the organogenic lines produced in the third stage. Optionally, the shoots regenerated in stages 2 or 4 may be separated and proliferated under several different regimes of plant growth regulators before induction of roots.

The shoots regenerated or proliferated may then be separated and transferred to a rooting medium. Individual plantlets with established root systems are then transferred into soil for further growth.

In a preferred embodiment of the present invention, IZEC from a Salvia species, preferably a *S. sclarea* cultivar (such as the sage lines Genotype 1007 or Genotype 705 which have a high frequency of regeneration), are cultured to provide organogenic lines or to regenerate whole plants via organogenesis.

The preferred explant is an IZEC explant, which is first cultured on a nutrient medium with auxin that induces organogenic tissues (an initiation medium). These tissues can then be proliferated on media containing auxin and cytokinin. organogenic lines are established via selection, isolation and continuous subculture of organogenic tissues. Shoots can be regenerated from the proliferated tissues and propagated in the presence of auxin, cytokinin and gibberellic acid ($GA_3$) (shoot initiation medium). Roots are preferably induced from regenerated shoots on rooting media containing low concentration of auxins.

A number of genetic and environmental factors affect plant regeneration. Use of genetically similar explants from similar environments assists in providing a consistent yield of regenerated plants. Consistent responses for organogenesis are difficult to obtain where explant donor plants are not grown in the same controlled environment. Immature zygotic embryo cotyledons obtained from multiple field-grown plants may differ genetically because they are derived from an insect-mediated and open-pollinated population. In vitro proliferation of organogenic tissues not only consistently provides tissues with the same genetic background for shoot initiation, but also minimizes the influence of environmental factors.

The developmental stage of IZEC used as explants affects the present Salvia regeneration process. The preferred stages of immature seeds providing IZEC range from one to four weeks after flowering or pollination, more preferably from two to three weeks after pollination when the color of the seeds turns to green from yellow-green and the embryo cotyledons become creamy white or yellow-green (FIG. 1). Intact seeds have been shown to produce more shoots in a number of species (U.S. Pat. No. 5,477,000 to Saxena and Malik) and may be used for shoot multiplication in Salvia in the present methods. However, the seed coat and embryonic axis are preferably removed and discarded in the present methods to eliminate shoot proliferation from existing shoot primordia and to promote shoot regeneration from the embryonic cotyledon tissues. This is more important when the regeneration system is used for genetic transformation and for creating somaclonal variation.

The IZEC explants are then placed on a basal culture medium containing at least one plant growth regulator (an initiation medium). The procedure of the current invention is not limited to any single basal culture medium. A number of commonly used media in plant tissue culture, including L2, MS and B5 (George et al., (1987) *Plant culture media*, Vol. 1, Exegentics Limited, Wilts. BA13 4QG, England) may be suitable although a modified MS medium (Murashige and Skoog (1962) *Physiologqia Plantarum* 15: 473–493), modified as shown in Table 1, is preferred at present. Auxins, including but not limited to 2,4-D and NAA, are used in the basal medium for the initiation of organogenic tissues or callus, with 2,4-D being preferred. The concentration of auxin should be high enough to promote cell division and to prevent germination of the embryo if any embryonic axis is not completely removed from the explant. The preferred range of 2,4-D concentrations is from 2 to 20 mg/L, more preferably between 2 to 5 mg/L. The auxin concentration should not be so high as to inhibit cell growth and cell division and kill the tissues, and preferably is not equal to or higher than 40 mg/L.

Although any orientation of the explant cotyledons may be used on the medium, preferably the abaxial side is placed in contact with the medium. The cultures are then incubated, for example at 25° C. with a 16 hour photoperiod (approx. 80 $\mu$E m$^{-2}$ s$^{-1}$), for about four to six weeks until organogenic tissues or callus are induced. After organogenic tissues or calli are initiated from the IZEC explant, the regenerated tissues may then be isolated and transferred to a proliferation medium. Any suitable proliferation medium may be used, such as MSO medium (Table 4) for three to four weeks and then BI medium (Table 4), or more preferably BI medium directly. (Note that some media described herein may be used for multiple purposes, e.g., BI medium may be used as a proliferation medium and as a shoot initiation medium, depending on the types of tissue used.) The proliferated organogenic tissues or calli may be isolated and subcultured on BI medium every three or four weeks to develop organogenic lines.

Shoots are obtained from the explant material as follows. Organogenic tissues regenerated on 2,4-D medium (and optionally further proliferated) are transferred to a suitable shoot initiation medium (see Table 5), preferably GBN, B5 or B02, for about four weeks, and then transferred to a medium with 5×GBN. Alternatively, organogenic lines (preferably white organogenic lines, and more preferably green organogenic lines) are transferred to 5×GBN medium or GEN medium. It is preferred to subculture the tissues on fresh shoot initiation media every three or four weeks until shoots are obtained.

Additionally, IZEC explants are cultured on BI medium (Table 5), and more preferably on BI (Table 5) or M5 (Table 5) medium for four weeks and then on 10×GBN medium to induce shoots. Continuous subculture of the tissues about every four weeks may be necessary to increase the number of shoots. Regenerated shoots can be proliferated and normalized on a number of media containing lower concentrations of plant growth regulators, including but not limited to GBN, BN, M5 and BIN, preferably BN and BIN (Tables 4 and 5). When a shoot has more than two leaves with a visible internode, it is then transferred to a different medium for root development.

A few of the shoots proliferating on BN and BIN (Table 4) media may produce roots, however, most of the shoots need to be transferred onto a root initiation medium which contains a low concentration of auxin (Table 6). The preferred root initiation medium contains indole butyric acid (IBA), preferably 0.2 mg/L IBA. A three to four hour desiccation of the shoots, for example in an open dry petri dish, before transferring to the root initiation medium may enhance root initiation. The resulting plantlets may be transferred into soil for further growth when roots are sufficiently developed, for example when the length of the root system exceeds 20 mm. A preferred soil mixture is Redi-Earth (Grace Sierra Horticultural Products Co.). The plant may be transferred into a greenhouse for more growth and for seed production when suitable, for example when the plant has developed four more leaves while in soil.

In another embodiment of the present methods, the Salvia IZEC explant is placed on an initiation medium containing a cytokinin (such as BA) and shoots are produced from the explant. The shoots are optionally separated and further proliferated. Shoots are transferred to a root initiation medium for the development of roots, to produce galvia plantlets.

The present methods are useful in providing plant material for use in producing genetically transformed sage. The frequency of plant regeneration in sage is affected by genotype of the original plant, the type and concentration of plant growth regulators in regeneration procedures, and the source of the explant tissues. As illustrated by the results provided herein (see, e.g. Table 3), large standard errors can be observed in regeneration techniques. Such results indicate that use of established organogenic lines (those known to provide high rates of regeneration) may be more efficient than direct use of IZECs from plants for transformation.

Regeneration of plants using the methods described above is an essential component of strategies used in the genetic modification of sage through the incorporation of transgenes. Such modifications may utilize genes which improve agronomic characteristics or performance of sage plants. Examples of such genes preferred in the present methods include those which provide resistance to pathogens of clary sage such as fungi (*Fusarium oxysporum, Rhizoctonia sp., Pythium sp.*) bacteria and viruses (sage yellow mosaic virus, cucumber mosaic virus). Other genes may be used to provide resistance to environmental stresses (e.g., to provide cold tolerance, drought tolerance or salt tolerance) or to provide resistance to particular herbicides or classes of herbicides. Still other genes may be used to alter the time required to reach the flowering stage, the proportion of floral tissue to vegetative tissue, the development of specific plant organs, or the yields of total biomass.

Other examples of genes preferred in the present methods include those which alter the temporal or spatial expression or absolute amounts of specific secondary metabolites. For example, genetic modifications may be made whereby sclareol is synthesized in tissues other than or in addition to trichomes. In another example, the synthesis of geranylgeranyl pyrophosphate (GGPP) may be enhanced through modification and reintroduction of a modified GGPP synthase gene. Alternatively, the biosynthesis of specific secondary metabolites may be reduced or abolished through the introduction of antisense genes.

Additional examples of genes useful in the present methods include those encoding enzymes that are not normally found in clary sage but which act on substrates (such as GGPP) that are found in clary sage; such a transgenic plant could be designed to biosynthesize valuable molecules that are not produced in clary sage plants in the absence of the introduced enzyme. For example a bacterial enzyme able to convert sclareol to sclareolide, when expressed in trichomes, would convert sclareol to sclareolide within the clary sage plant. In another example, taxadiene synthase, which utilizes GGPP as substrate, allows the synthesis of taxadiene, the committed precursor of taxol.

Any strain of Agrobacterium suitable for the transformation of clary sage can be used in the methods of the present invention. In particular, strains of *Agrobacterium tumefaciens* designated A281, C58 and LBA4404 are useful for transforming clary sage. The binary vector pRI 121 containing the selectable marker gene NPT II under the control of a nos promoter and terminator, and the reporter gene beta-glucuronidase (GUS) under the control of a CaMV 35S promoter and nos terminator, is useful in the present methods. Additionally, the vector designated pIDK8 is also useful in the present methods; this vector contains the selectable marker gene NPT II under the control of a nos promoter and terminator, and the reporter gene chloramphenicol acetyltransferase (CAT) under the control of a CaMV 35S promoter and pea rbc-S terminator. Electroporation is a useful method to introduce the binary vector into an *Agrobacterium tumefaciens* strain such as A281, C58 or LBA4404. Electroporated Agrobacterium are then selected, for example on LB medium containing kanamycin and rifampicin. Single transformed colonies are isolated and analyzed for the presence of the binary vector using restriction endonucleases, using techniques known in the art. Fresh cultures of Agrobacterium containing the desired vector are then used for inoculation of organogenic lines. Transformants of clary sage then can be selected, for example, using organogenic proliferation and shoot initiation media containing kanamycin and cefotamin. Selected transformants can then be analyzed for expression of reporter gene products, such as NPT II and GUS (where the binary vector pBI 121 was utilized) or NPT II and CAT (where the pIDK8 vector was utilized). Transformed clary sage plants can then be regenerated via organogenesis and tissue culture techniques according to the methods of the present invention.

Transformation of plant cells may be conducted using organogenic tissues or callus produced by the present methods (which transformed cells are then proliferated to form transformed organogenic tissues). Alternatively, isolated IZEC tissues can first be transformed and then regenerated using the present methods.

In view of the foregoing, a further aspect of the present invention is a method of providing recombinant Salvia plants comprising transformed plant cells. Any suitable method of transforming plant cells may be used in the present methods. The transformed plant cells contain a heterologous DNA construct which may, for example, be an expression cassette comprising, in the 5' to 3' direction, a promoter, a structural gene positioned downstream from the promoter and operatively associated therewith, and a termination sequence positioned downstream from the structural gene and operatively associated therewith. The method comprises obtaining IZEC or organogenic explants from Salvia species, transforming the cells of the explant with heterologous DNA, and regenerating recombinant plants from said transformed explant material.

Structural genes are those portions of genes which comprise a DNA segment coding for a protein, polypeptide, or portion thereof, possibly including a ribosome binding site and/or a translational start codon, but lacking a promoter. The term can also refer to copies of a structural gene naturally found within a cell but artificially introduced. The structural gene may encode a protein not normally found in the plant cell in which the gene is introduced or in combination with the promoter to which it is operationally associated, or may encode additional amounts of a protein which is also normally found in the plant cell. Genes which may be operationally associated with a promoter of the present invention for expression in a plant species may be derived from a chromosomal gene, cDNA, a synthetic gene, or combinations thereof. Structural genes which are preferred in the present methods include those which affect sclareol production in the sage plant, but include other heterologous genes such as those encoding anti-pathogen proteins or those regulating biosynthesis of secondary metabolites (e.g., such as those involving metabolism of geranyl geranyl pyrophosphate(GGPP)).

The term "operatively associated," as used herein, refers to DNA sequences on a single DNA lo molecule which are associated so that the function of one is affected by the other. Thus, a promoter is operatively associated with a structural gene when it is capable of affecting the expression of that structural gene (i.e., the structural gene is under the transcriptional control of the promoter). The promoter is said to be "upstream" from the structural gene, which is in turn said to be "downstream" from the promoter. All regulatory regions should be capable of operating in the cells of the tissue to be transformed. The 3' termination region may be derived from the same gene as the transcriptional initiation region or may be derived from a different gene.

Where the expression product of the structural gene is to be located in a cellular compartment other than the cytoplasm, the structural gene may be constructed to include regions which code for particular amino acid sequences which result in translocation of the product to a particular site, such as the cell plasma membrane, or may be secreted into the periplasmic space or into the external environment of the cell. Various secretory leaders, membrane integration sequences, and translocation sequences for directing the peptide expression product to a particular site are described in the literature. See, for example, Cashmore et al., *Bio/Technology* 3, 803–808 (1985), Wickner and Lodish, *Science* 230, 400–407 (1985).

Any suitable method may be used to transform Salvia cells in the methods of the present invention. Such vectors include viral vectors, Agrobacterium-derived vectors and ballistic vectors, as are known in the art. *Agrobacterium tumefaciens* cells containing a DNA construct, wherein the DNA construct comprises a Ti plasmid, are useful in methods of making transformed plants as is known in the art. Plant cells are infected with an *Agrobacterium tumefaciens* as described above to produce a transformed plant cell, and then a plant is regenerated from the transformed plant cell. Numerous Agrobacterium-derived vector systems are known. For example, U.S. Pat. No. 4,459,355 discloses a method for transforming susceptible plants, including dicots, with an Agrobacterium-derived strain containing the Ti plasmid. The transformation of woody plants with an Agrobacterium vector is disclosed in U.S. Pat. No. 4,795,855. Further, U.S. Pat. No. 4,940,838 to Schilperoort et al. discloses a binary Agrobacterium-derived vector (i.e., one in which the Agrobacterium contains one plasmid having the vir region of a Ti plasmid but no T region, and a second plasmid having a T region but no vir region) useful in carrying out the present invention.

Microparticles carrying a transforming DNA construct, which microparticle is suitable for the ballistic transformation of a plant cell, are also useful for making transformed plants according to the present invention. The microparticle is propelled into a plant cell to produce a transformed plant cell, and a plant is regenerated from the transformed plant cell. Any suitable ballistic cell transformation methodology and apparatus can be used in practicing the present invention, as may be known in the art. Exemplary apparatus and procedures are disclosed in Sanford and Wolf, U.S. Pat. No. 4,945,050, and in Agracetus European Patent Application Publication No. 0 270 356, titled *Pollen-mediated Plant Transformation*. When using ballistic transformation procedures, the expression cassette may be incorporated into a plasmid capable of replicating in the cell to be transformed. Examples of microparticles suitable for use in such systems include 1 to 5 $\mu$m gold spheres. The DNA construct may be deposited on the microparticle by any suitable technique, such as by precipitation.

An exemplary method for transforming clary sage involves the use of *Agrobacterium tumefaciens*. The binary vector pBI 121 contains the selectable marker gene NPT II under the control of a nos promoter and terminator, and the reporter gene beta-glucuronidase (GUS) under the control of a CaMV 35S promoter and nos terminator. The vector designated pIDK8 contains the selectable marker gene NPT II under the control of a nos promoter and terminator, and the reporter gene chloramphenicol acetyltransferase (CAT) under the control of a CaMV 35S promoter and pea rbc-S terminator. Electroporation is used to introduce the binary vector into *Agrobacterium tumefaciens*. Electroporated Agrobacterium are then selected on LB medium containing kanamycin and rifampicin. Single transformed colonies are isolated and analyzed for the presence of the binary vector using restriction endonucleases, as is known in the art. Clary sage organogenic lines are then inoculated with fresh cultures of Agrobacterium containing either the vector pBI 121 or pIDK8. Transformants of clary sage are then selected using organogenic proliferation and shoot initiation media containing kanamycin and cefotamin. Selected transformants are analyzed for expression of the reporter gene products (NPT II and GUS in plants transformed with vector pBI 121; NPT II and CAT in plants transformed with vector pIDK8). Transformed clary sage plants are then regenerated via organogenesis and tissue culture techniques according to the methods of the present invention, to provide transformed organogenic lines.

The following examples are provided to illustrate the present invention, and should not be construed as limiting thereof. In these examples, IZEC means immature zygotic embryo cotyledons; $\mu$E means micro Einstein; BA means $N^6$-benzyladenine; $GA_3$ means gibberellic acid; IAA means indole-3-acetic acid; IBA means indole butyric acid; NAA means 2-naphthylacetic acid; 2,4-D means 2,4-dichlorophenoxyacetic acid; and fpm means feet per minute.

EXAMPLE 1

Organogenic Tissue Initiation

Seeds of four genetic lines of clary sage (lines 308, 705, 1004 and 1007) were obtained and sage plants were grown in pots with Redi-Earth (Grace Sierra Horticultural Products Co.) in a greenhouse environment. About six to eight weeks after germination, the plants were vernalized in a growth chamber at 8° C. in the light (approximately 20 $\mu$E m$^{-2}$ S$^{-1}$ from cool-white fluorescent lamps, Sylvania, Danvers, Mass., USA) and 3° C. in the dark with a nine hour photoperiod for eight to ten weeks. After flowering, a human-facilitated pollination process was carried out by transferring pollens in broken anthers on to stigmata to facilitate seed production. About two to three weeks after pollination, the immature seeds within calyces were harvested to provide IZEC.

An additional source of IZEC were sage plants grown in the field. The inflorescence with one- to four-week old immature seeds was harvested to provide IZEC. Excess immature seeds on the inflorescence were stored in a plastic bag at 4° C. for further use.

The calyces containing immature seeds were harvested from inflorescence and surface-sterilized with 70% 2-propanol for 2 minutes, placed in 1% sodium hypochlorite (20% CLOROX® bleach) for 15 minutes, and rinsed (4 times) in sterile water. The calyces from field-grown plants were rinsed with water before sterilization. Immature seeds were aseptically removed from the calyces and dissected.

Immature embryos were removed from the seed coat and embryo axes were cut and discarded. The cotyledons were wounded with a dissection blade or forceps and placed abaxial side down on modified MS basal media (Table 1) with different plant growth regulators for organogenic tissue initiation. The plant growth regulators and their concentrations used in the media for organogenic tissue initiation are listed in Table 2.

TABLE 1

Composition of modified MS basal medium

| Compound* | Concentration (mg/liter) |
|---|---|
| Ammonium nitrate | 1650 |
| Potassium nitrate | 1900 |
| Potassium phosphate monobasic | 170 |
| Magnesium sulfate | 180.7 |
| Calcium chloride anhydrous | 332.2 |
| Boric acid | 6.2 |
| Cobalt chloride.6H$_2$O | 0.025 |
| Cupric sulfate.5H$_2$O | 0.025 |
| Na$_2$-EDTA | 37.26 |
| Ferrous sulfate.7H$_2$O | 27.8 |
| Manganese sulfate.H$_2$O | 16.9 |
| Molybdic acid(Na-salt).2H$_2$O | 0.25 |
| Potassium iodide | 0.83 |
| Zinc sulfate.7H$_2$O | 8.6 |
| Myo-inositol | 100 |
| Thiamine-HCl | 10 |
| Nicotinic acid | 1 |
| Pyridoxine-HCl | 1 |
| Sucrose | 30000 |
| Phytagel | 200 |

*The composition of *Salvia sclarea* basal culture medium containing salts of modified MS (Murashige and Skoog 1962) medium and B5 vitamins (Gamborg et al., 1968) from Sigma Chemical Co., St. Louis, MO, USA.

TABLE 2

Plant growth regulators and the concentration used for organogenic tissue initiation.

| Name | Basal Medium[1] | Growth Regulator[2] | Concentration (mg/L) |
|---|---|---|---|
| D2 | Modified MS | 2,4-D | 2.0 |
| D4 | Modified MS | 2,4-D | 4.0 |
| D5 | Modified MS | 2,4-D | 5.0 |
| D10 | Modified MS | 2,4-D | 10.0 |
| D20 | Modified MS | 2,4-D | 20.0 |
| D40 | Modified MS | 2,4-D | 40.0 |
| N5 | Modified MS | NAA | 5.0 |
| N10 | Modified MS | NAA | 10.0 |

[1]pH = 5.8 before sterilization; all media were solidified with 0.2% Phytagel.
[2]From Sigma Chemical Co., St. Louis, MO, USA; filter sterilized and added after autoclave.

Figure 2B:
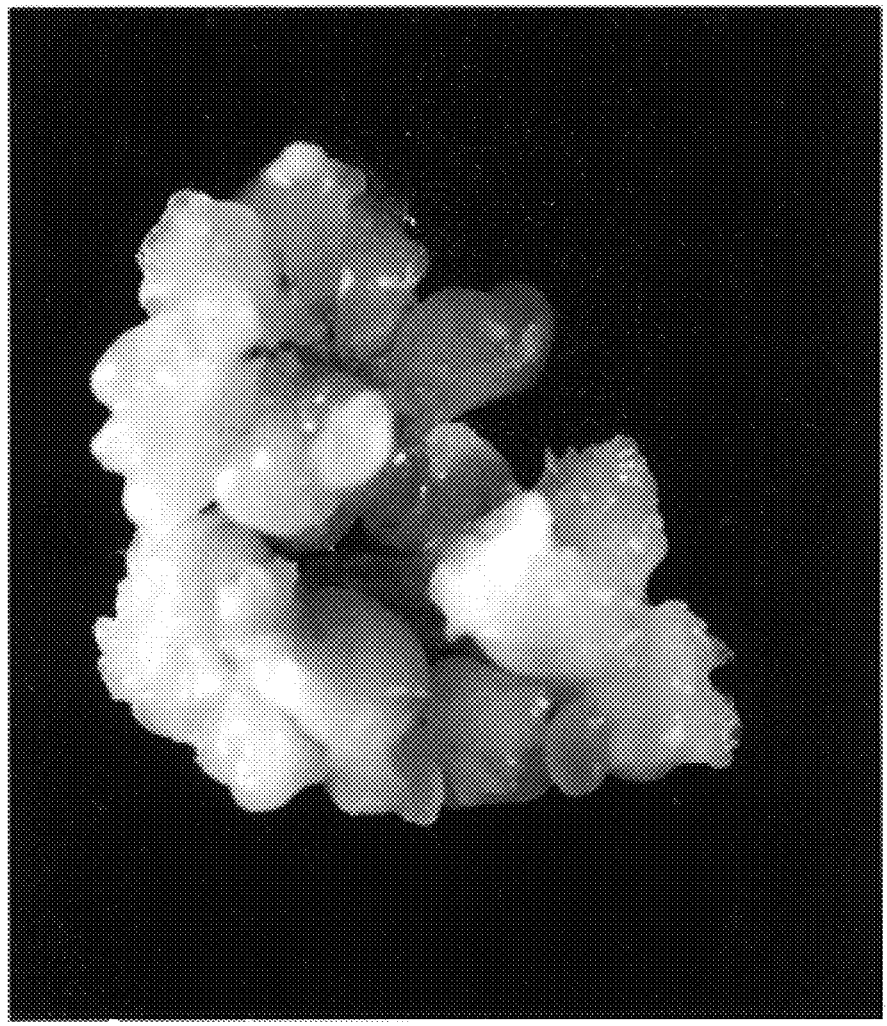
FIG. 2b depicts organogenic *S. sclarea* tissues proliferating on MSO medium.

The cotyledons on the media were incubated at 25° C. with a 16 hour photoperiod (from cool-white fluorescent lamps, Sylvania, Danvers, Mass., USA; approx. 80 μE m$^{-2}$ s$^{-1}$). After four to six weeks, most of the explants gave rise to organogenic tissues and callus. An example of typical organogenic tissues and callus regenerated on 2,4-D containing media is presented in FIG. 2a. The organogenic tissues, in general, were compact, globular and organized tissues with a smooth and shining surface. Although they were morphologically similar to early stage somatic embryos (Liu et al., (1992) *In Vitro Cell. Dev. Biol.* 28P:153–160), these tissues did not produce mature somatic embryos when they were subcultured on a medium without plant growth regulators (MSO) or on fresh regeneration medium (2, 4-D). Instead, these tissues proliferated and developed into structures similar to shoot buds (FIG. 2b).

A higher frequency of organogenic tissue initiation was observed from clary sage lines 705 and 1007 on the media containing 2 mg/L of 2,4-D (Table 3). As the concentration of 2,4-D increased, the percentage of IZEC giving rise to organogenic tissues decreased. organogenic tissues only sporadically regenerated on the medium containing 20 mg/L of 2,4-D. The explants cultured on 40 mg/L 2,4-D did not produce any regenerated tissues and died after four weeks on the medium.

The IZEC from the immature seeds stored at 4° C. for one to ten days gave rise to organogenic tissues at a frequency comparable to those from fresh IZEC.

Figure 3:
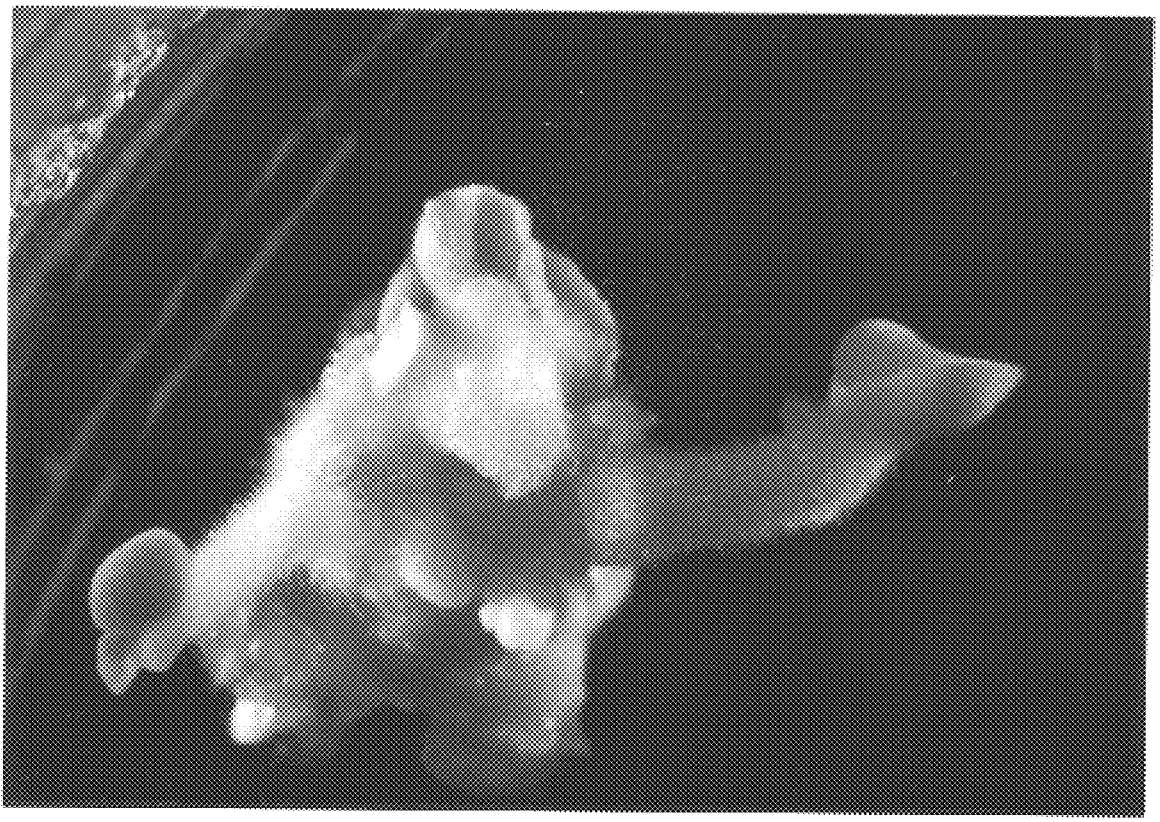
FIG. 3 shows somatic *S. sclarea* embryos regenerated from IZEC.

IZEC cultured on medium containing 5 or 10 mg/L NAA gave rise to a few horn-shaped somatic embryos from more than 100 cotyledons (FIG. 3). Most of the explants produced a large number of roots. These treatments (i.e., use of 5 or 10 mg/L NAA) did not result in organogenic or somatic embryogenic tissues which could be proliferated under the conditions used.

IZECs from yellow-green immature seed (less than two weeks after pollination) and from white and white-brown immature seeds (more than three weeks after pollination) occasionally gave rise to organogenic tissues but at a very low frequency.

TABLE 3

Percent of immature zygotic embryo cotyledons (IZEC) producing organogenic tissues

| | Concentration of 2,4-D (mg/L) | | | |
|---|---|---|---|---|
| Genotype | 2 | 4 | 5 | 10 |
| 1007 | 56.3 ± 20.9 | 19.5 ± 16.5 | 0.0 ± 0.0 | 8.9 ± 11.7* |
| 1004 | 11.0 ± 7.9 | 15.0 ± 15.2 | 18.9 ± 6.9 | 5.5 ± 7.28 |
| 705 | 68.8 ± 7.9 | 20.0 ± 12.1 | 4.9 ± 5.2 | 3.7 ± 3.1 |
| 308 | 11.3 ± 4.7 | 7.8 ± 6.8 | 0.0 ± 0.0 | 1.3 ± 2.5 |

*Where the standard error is larger than the mean, more than two replications did not give rise to organogenic tissues.

TABLE 4

Plant growth regulators and concentration used for organogenic tissue proliferation

| Name | Basal Medium[1] | Growth Regulator[2] (mg/L) |
|---|---|---|
| MSO | Modified MS | — |
| M5 | Modified MS | BA (1.2) |
| BI | Modified MS | BA (5.0) + IAA (0.5) |
| BN | Modified MS | BA (2.0) + NAA (0.1) |
| BIN | Modified MS | BA (0.2) + IAA (0.1) + NAA (0.1) |

[1]pH = 5.8 before sterilization; all media were solidified with 0.2% Phytagel.
[2]From Sigma Chemical Co., St. Louis, MO, USA; filter sterilized and added after autoclave.

EXAMPLE 2

Organogenic Tissue Proliferation and Development of Organogenic Cell Lines

Figure 9:
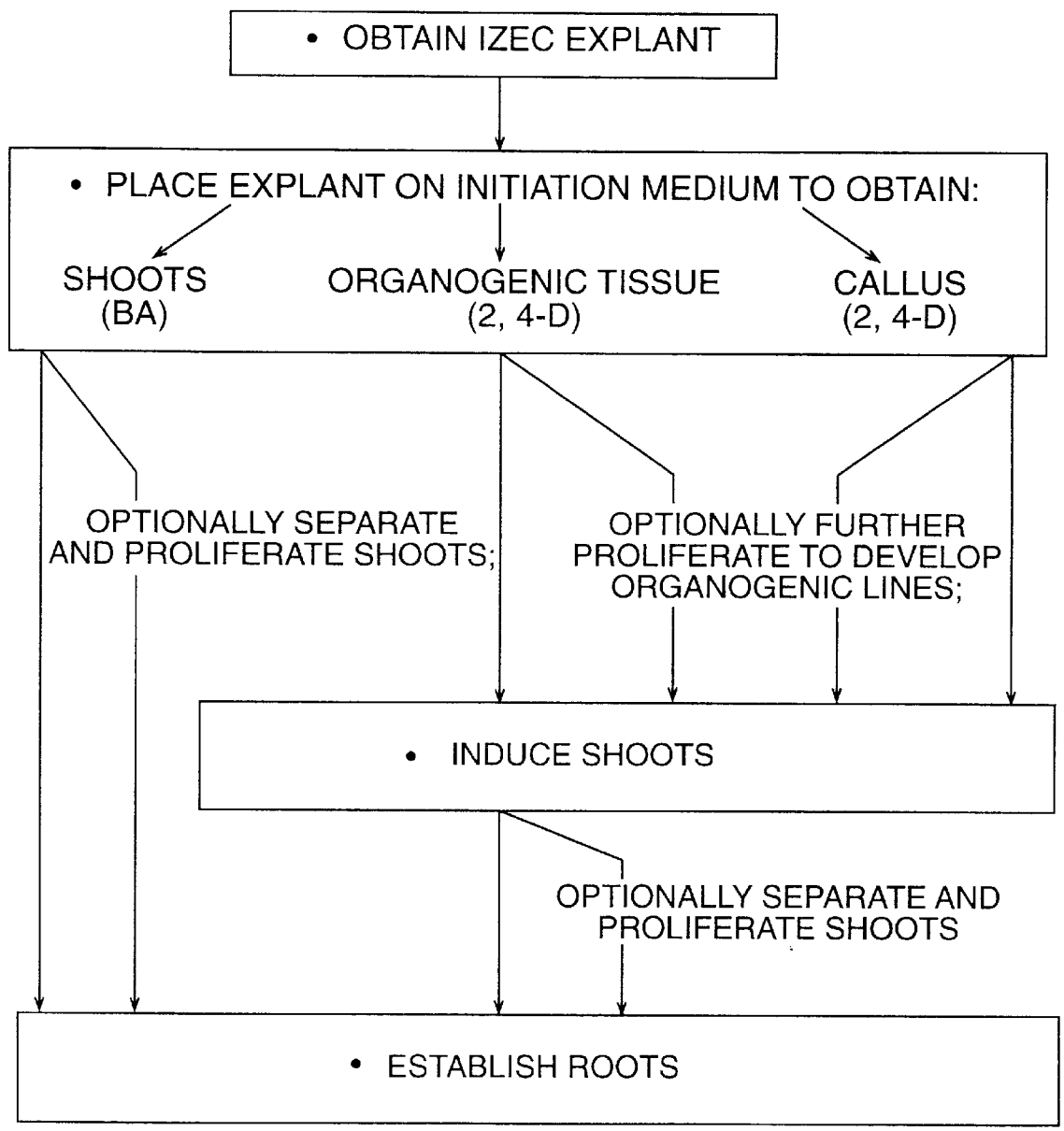
FIG. 9 is a flow chart depicting the various pathways to regenerate Salvia using the present methods.

Organogenic tissues induced from IZEC on 2,4-D containing media (Example 1) were transferred to a medium for proliferation. As shown in FIG. 9, use of 2,4-D gives rise to both organogenic tissues and callus on the same explant (see FIG. 2A); these tissues can be separated and transferred separately to the proliferation medium. The organogenic tissue proliferation medium was BI which contained 5 mg/L of BA and 0.5 mg/L of IAA (Table 4). After about four weeks on BI medium, most of the tissues proliferated were green, globular and shoot bud-like structures, called green organogenic tissues (FIG. 4a). Some of the proliferated tissues still remained white and globular with a shining surface, called white organogenic tissues (FIG. 4b), similar to the organogenic tissues induced on 2,4-D containing media. These two kinds of tissues were then separated and subcultured on fresh BI medium. The white organogenic tissues continued to produce these two types of tissues. The green organogenic tissues generated primarily more green shoot bud-like structures with some leafy structures and callus. Upon continuous subculture, the callus gave rise to more callus (FIG. 5) and some shoot bud-like structure. These three types of tissues were subcultured about every four weeks to proliferate organogenic tissues.

White organogenic tissues isolated from tissues proliferating on BI medium were subcultured on either BN, BIN, MSO or D20 media (Tables 2 and 4) for about four weeks; only white organogenic tissues proliferated. After continuous subcultures on these media, particularly MSO and D20, the white organogenic tissues became brown and lost the potential to proliferate and regenerate. However, a four-week subculture on BN or BIN medium between two passages of subculture on BI medium was more efficient to scale up white organogenic tissues.

EXAMPLE 3

Shoot Initiation and Proliferation

Sage shoots were initiated from three types of tissues: 1) organogenic tissues induced on 2,4-D containing media, 2) proliferated organogenic lines and 3) IZEC. The compositions of shoot initiation media are listed in Table 5.

Organogenic tissues induced by 2,4-D were isolated and transferred to GBN or 5×GBN medium (Table 5). After about three weeks of culture on these media, a majority of the tissues produced loose white callus with some green shoot bud-like structures. Isolation and continuous subculture of the green shoot bud-like structures on the same medium resulted in shoot regeneration.

Additionally, organogenic tissues were first transferred to B02 medium (Table 5) for about four weeks, and then transferred and subcultured on 5×GBN (Table 5). The four-week subculture on B02 reduced callus production and increased the frequency of shoot regeneration on 5× GBN medium.

Organogenic lines (including green organogenic tissues, white organogenic tissues and callus with dark-green centers) produced shoots after transfer and continuous subculture on B5, GBN or 5× GBN medium (Table 5). Most of the green organogenic tissues with shoot-bud-like structures gave rise to shoots within about four weeks on B5, GEN or 5× GBN medium. In general, the white organogenic tissues and callus had to be subcultured more than one passage, each passage of about four weeks, on B5, GBN or 5×GBN in order to induce shoots.

In addition, shoots were induced from the organogenic lines on 10×GBN (Table 5). However, continuous subculture on this medium resulted in deterioration and death of the tissues. A few shoots were also regenerated from organogenic lines during their proliferation on BI medium.

Figure 7A:
FIGS. 7(a and b) show direct *S. sclarea* shoot regeneration from an immature zygotic embryo cotyledon (IZEC) on BI medium.
Figure 7B:

When IZEC were placed on BI or M5 media (Table 4), the tissues became green and enlarged after about one week. About two weeks after culture on BI medium, some dark green centers developed, with a few shoots regenerated from the tissues (FIG. 7a). Continuous subculture of the tissues with dark-green centers on 10×GBN and then GEN (Table 5) resulted in more shoot regeneration (FIG. 7b).

Regenerated sage shoots were proliferated on a number of media, including MSO, GBN, 5×GBN, M2, BG, GB, BING, BN, and BIN (Tables 4 and 5). On the basal medium without plant growth regulators (MSO), only a few new shoots proliferated from each shoot although they were morphologically more normal. The addition of 0.2 mg/L to 1 mg/L of BA in the basal medium resulted in proliferation of more shoots. $GA_3$ in the range of 0.1 to 2.5 mg/L in the media (GBN, 5×GBN, M2, GB, BG, BING) not only promoted shoot and leaf elongation but also enhanced proliferation of even more shoots. However, shoots proliferated on $GA_3$ containing medium for more than two weeks were more abnormal with thin and elongated stems and leaves. Although a large number of more normal shoots were proliferated on BN and BIN, subculture of the shoots without visible internodes on M2 for two weeks resulted in elongation of the shoots.

TABLE 5

Plant growth regulators and the concentration used for shoot initiation and proliferation.

| Name | Basal Medium[1] | Growth Regulator[2] (mg/L) |
|---|---|---|
| BO2 | Modified MS | BA(0.2) |
| M5 | Modified MS | BA(1.2) |
| B5 | Modified MS | BA(5.0) |
| BI | Modified MS | BA(5.0) + IAA(0.5) |
| M2 | Modified MS | $GA_3$(2.0) + BA(0.1) |
| GBN | Modified MS | $GA_3$(0.5) + BA(0.2) + NAA(0.1) |
| 5 × GBN | Modified MS | $GA_3$(2.5) + BA(1.0) + NAA(0.5) |
| 10 × GBN | Modified MS | $GA_3$(2.5) + BA(2.0) + NAA(1.0) |
| BG | Modified MS | $GA_3$(1.0) + BA(1.0) |
| GB | Modified MS | $GA_3$(0.5) + BA(2.0) |
| BING | Modified MS | $GA_3$(0.1) + BA(0.2) + IAA(0.1) + NAA(0.1) |

[1]pH = 5.8 before sterilization; all media were solidified with 0.2% Phytagel.
[2]From Sigma Chemical Co., St. Louis, MO, USA; filter sterilized and added after autoclave.

EXAMPLE 4

Root Initiation

Roots were sporadically initiated at very low frequency from the shoots proliferating on BN and BIN (Table 4) for five to six weeks without subculture on fresh media. The majority of shoots had to be transferred to a medium containing a low concentration of auxin. The auxins and their concentrations used for root induction are listed in Table 6.

TABLE 6

Plant growth regulators and the concentration used for root initiation.

| Medium Name[1] | Growth Regulator[2] (mg/L) |
|---|---|
| M3 | NAA (0.2) |
| IAA | IAA (0.2) |
| IBA | IBA (0.2) |
| R1 | IAA (1.0) + BA (0.2) |
| R2 | IAA (1.0) + NAA (0.2) + BA (0.2) |
| IN | IAA (0.1) + NAA (0.2) |
| IB | IAA (0.5) + BA (0.2) |
| INB | IAA (0.5) + NAA (0.1) + BA (0.2) |

[1]pH = 5.8 before sterilization; all media were solidified with 0.2% Phytagel; basal medium was modified MS.
[2]From Sigma Chemical Co, St. Louis, MO, USA; filter sterilized and added after sterilization.

Figure 8:
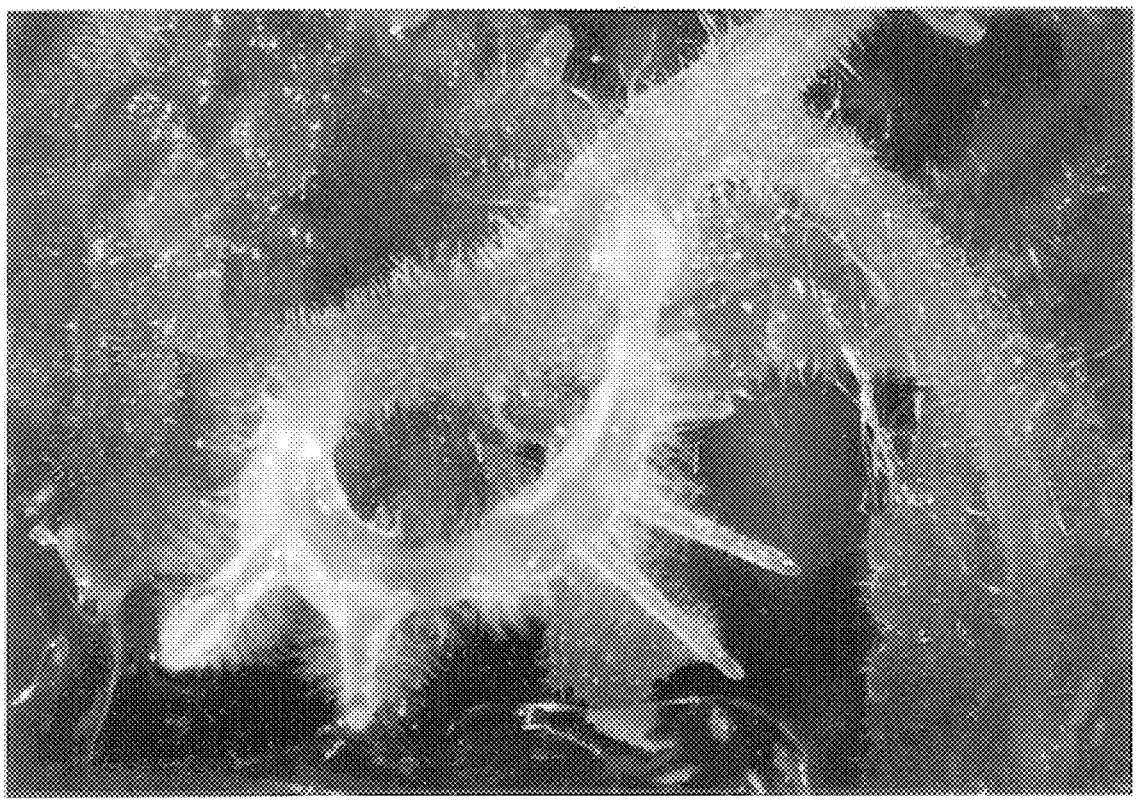
FIG. 8 depicts roots initiated from a regenerated *S. sclarea* shoot.

Roots were induced at a low frequency on M3, IAA, IN, IB and INB media (Table 4 and FIG. 8). No roots were induced from shoots cultured on R1 and R2 (Table 6). Higher concentrations of IAA in the media promoted callus proliferation from the bottom of the shoots. Callus proliferation not only resulted in the arrest of shoot growth, but also promoted deterioration of the shoots. Most of the roots induced on these media were thin and brown-white, and the survival rate of plantlets with this kind of root system was less than 10% after transfer into soil. Among the auxins tested, IBA at 0.2 mg/L promoted more and stronger root formation, especially in combination with one half strength of modified MS basal medium solidified with 0.7% of Phytoagar (GIBCO BRL, Grand Island, N.Y., USA).

Desiccation of regenerated shoots before transfer to IBA medium increased the frequency of stronger root formation. Individual shoots were isolated and transferred to a 100×25 mm dry petri dish. The petri dish was open and placed in an sterile laminar flow hood (The Baker Company, Sanford, Me., USA) with an average air flow velocity of about 100 fpm. After about three to four hours, when the tissues became soft to the touch with a pair of forceps, the shoots were transferred to IBA medium and incubated at 25° C. with a 16 hour photoperiod as described in Example 1. Thicker white roots were observed as early as two days after culture on IBA medium. The roots induced by the combination of desiccation and IBA also grew faster.

After the roots reached more than 20 mm in length, the medium was washed away with water and the plantlets transferred into a pot containing Redi-Earth soil mix. The pot was covered with a Phytatray lid (Sigma chemical Co., St. Louis, Mo., USA) to retain a high humidity condition for about two weeks. After plants developed four more leaves while in soil, they were transferred to the greenhouse for additional growth and R1 seed production.

The foregoing is illustrative of the present invention and is not to be construed as limiting thereof. The invention is defined by the following claims, with equivalents of the claims to be included therein.

That which is claimed is:

1. A method of producing organogenic tissues from a plant of the genus Salvia, comprising:

a) obtaining an immature zygotic embryo cotyledon (IZEC) explant of a Salvia plant; and b) culturing said explant on an initiation medium comprising nutrients and at least one plant growth regulator comprising auxin so as to produce organogenic tissues.

2. The method of claim 1, further comprising culturing said organogenic tissues on a shoot initiation medium so as to produce at least one shoot.

3. The method of claim 2, further comprising culturing said shoot on a rooting medium so as to produce at least one root.

4. The method of claim 1 wherein said plant growth regulator is 2-naphthylacetic acid (NAA) or 2,4-dichlorophenoxyacetic acid (2,4-D).

5. The method of claim 1 wherein said plant growth regulator is 2,4-dichlorophenoxyacetic acid (2,4-D) in an amount of from about 2 mg/L to about 20 mg/L.

6. The method of claim 1 wherein at least one cell of said IZEC is transformed with a heterologous DNA molecule prior to culturing.

7. The method of claim 1 further comprising transforming at least one cell of said organogenic tissues obtained in step (b) with a heterologous DNA molecule.

* * * * *